United States Patent
Hodorek et al.

(10) Patent No.: US 10,271,955 B2
(45) Date of Patent: Apr. 30, 2019

(54) ACL ACCOMMODATING TIBIAL DESIGN

(71) Applicant: Zimmer, Inc., Warsaw, IN (US)

(72) Inventors: Robert Hodorek, Warsaw, IN (US); Herve Windisch, Winterthur (CH); Marc Bandi, Winterthur (CH); Thomas Trachsler, Kefikon (CH)

(73) Assignee: Zimmer, Inc., Warsaw, IN (US)

( * ) Notice: Subject to any disclaimer, the term of this patent is extended or adjusted under 35 U.S.C. 154(b) by 123 days.

(21) Appl. No.: 15/427,280

(22) Filed: Feb. 8, 2017

(65) Prior Publication Data
US 2017/0143497 A1    May 25, 2017

Related U.S. Application Data

(60) Continuation of application No. 14/487,730, filed on Sep. 16, 2014, now Pat. No. 9,585,759, which is a
(Continued)

(51) Int. Cl.
*A61F 2/38* (2006.01)
*A61B 17/16* (2006.01)
(Continued)

(52) U.S. Cl.
CPC .......... *A61F 2/389* (2013.01); *A61B 17/1675* (2013.01); *G06F 19/00* (2013.01); *A61B 17/1764* (2013.01); *A61F 2002/30006* (2013.01); *A61F 2002/3007* (2013.01); *A61F 2002/3011* (2013.01); *A61F 2002/30011* (2013.01); *A61F 2002/30013* (2013.01); *A61F 2002/30014* (2013.01); *A61F 2002/3092* (2013.01); *A61F 2002/30112* (2013.01); *A61F 2002/30131* (2013.01); *A61F 2002/30934* (2013.01); *A61F 2002/3895* (2013.01); *A61F 2230/0002* (2013.01); *A61F 2230/0004* (2013.01); *A61F 2230/0013* (2013.01); *A61F 2250/0018* (2013.01); *A61F 2250/0024* (2013.01); *A61F 2310/00023* (2013.01);
(Continued)

(58) Field of Classification Search
CPC ...................................................... A61F 2/389
USPC ........................................... 623/20.32–20.33
See application file for complete search history.

(56) References Cited

U.S. PATENT DOCUMENTS 3,728,742 A    4/1973  Averill et al.
3,816,855 A    6/1974  Saleh
(Continued)

FOREIGN PATENT DOCUMENTS

EP    0672397 A1    9/1995
EP    3166541 B1    4/2018
(Continued)

OTHER PUBLICATIONS

"U.S. Appl. No. 13/001,442, Examiner Interview Summary dated Dec. 6, 2013", 3 pgs.
(Continued)

*Primary Examiner* — Olivia C Chang
(74) *Attorney, Agent, or Firm* — Schwegman Lundberg & Woessner, P.A.

(57) ABSTRACT

Surgical methods and tibial implants for accommodating the anterior cruciate ligament during unicompartmental or bi-unicompartmental knee arthroplasty procedures.

18 Claims, 6 Drawing Sheets

Related U.S. Application Data division of application No. 13/001,442, filed as application No. PCT/US2009/048205 on Jun. 23, 2009, now Pat. No. 8,864,836.

(60) Provisional application No. 61/076,206, filed on Jun. 27, 2008.

(51) Int. Cl.
*G06F 19/00* (2018.01)
*A61F 2/30* (2006.01)
*A61B 17/17* (2006.01)

(52) U.S. Cl.
CPC ............... *A61F 2310/00029* (2013.01); *A61F 2310/00095* (2013.01); *A61F 2310/00101* (2013.01); *A61F 2310/00131* (2013.01); *A61F 2310/00179* (2013.01)

(56) References Cited

U.S. PATENT DOCUMENTS

| | | | |
|---|---|---|---|
| 4,728,332 | A | 3/1988 | Albrektsson |
| 5,282,861 | A | 2/1994 | Kaplan |
| 5,282,868 | A | 2/1994 | Bahler |
| 5,824,101 | A | 10/1998 | Pappas |
| 5,954,768 | A | 9/1999 | Lepaih |
| 7,060,101 | B2 | 6/2006 | O'Connor et al. |
| 7,758,652 | B2 | 7/2010 | Engh et al. |
| 7,846,376 | B2 | 12/2010 | Abt et al. |
| 7,918,382 | B2 | 4/2011 | Charlebois et al. |
| 8,066,776 | B2 | 11/2011 | O'Connor et al. |
| 8,608,049 | B2 | 12/2013 | Hippensteel et al. |
| 8,728,086 | B2 | 5/2014 | Smith et al. |
| 8,864,836 | B2 | 10/2014 | Hodorek |
| 9,757,243 | B2 | 9/2017 | Jones et al. |
| 2002/0022890 | A1 | 2/2002 | Jacobsson et al. |
| 2004/0039447 | A1 | 2/2004 | Simon et al. |
| 2005/0143831 | A1 | 6/2005 | Justin et al. |
| 2006/0224244 | A1 | 10/2006 | Thomas et al. |
| 2006/0235517 | A1 | 10/2006 | Hodorek |
| 2007/0173858 | A1 | 7/2007 | Engh et al. |
| 2010/0016980 | A1 | 1/2010 | Donno et al. |
| 2011/0190898 | A1 | 8/2011 | Lenz et al. |
| 2011/0264097 | A1 | 10/2011 | Hodorek et al. |
| 2012/0035736 | A1 | 2/2012 | O'Connor et al. |
| 2012/0125896 | A1 | 5/2012 | Vargas et al. |
| 2012/0310361 | A1 | 12/2012 | Zubok et al. |
| 2013/0197527 | A1 | 8/2013 | Nadzadi et al. |
| 2014/0296990 | A1 | 10/2014 | Shaw et al. |
| 2014/0324178 | A1* | 10/2014 | Irwin .................. A61F 2/389 623/20.32 |
| 2015/0005889 | A1 | 1/2015 | Hodorek et al. |
| 2016/0008136 | A1* | 1/2016 | Jones .................. A61F 2/389 623/20.17 |

FOREIGN PATENT DOCUMENTS

| | | |
|---|---|---|
| FR | 2737970 | 2/1997 |
| WO | WO-2007090784 A1 | 8/2007 |
| WO | WO-2009158318 A1 | 12/2009 |
| WO | WO-2016007304 A1 | 1/2016 |

OTHER PUBLICATIONS

"U.S. Appl. No. 13/001,442, Final Office Action dated Aug. 30, 2013", 8 pgs.
"U.S. Appl. No. 13/001,442, Non Final Office Action dated Apr. 29, 2013", 7 pgs.
"U.S. Appl. No. 13/001,442, Notice of Allowance dated Jun. 24, 2014", 7 pgs.
"U.S. Appl. No. 13/001,442, Response filed Apr. 15, 2013 to Restriction Requirement dated Feb. 15, 2013", 12 pgs.
"U.S. Appl. No. 13/001,442, Response filed Jul. 29, 2013 to Non Final Office Action mailed Apr. 29, 2013", 17 pgs.
"U.S. Appl. No. 13/001,442, Response filed Dec. 2, 2013 to Final Office Action dated Aug. 30, 2013", 17 pgs.
"U.S. Appl. No. 13/001,442, Restriction Requirement dated Feb. 15, 2013", 10 pgs.
"U.S. Appl. No. 14/487,730, Corrected Notice of Allowance dated Feb. 2, 2017", 4 pgs.
"U.S. Appl. No. 14/487,730, Non Final Office Action dated Jun. 28, 2016", 10 pgs.
"U.S. Appl. No. 14/487,730, Notice of Allowance dated Oct. 25, 2016", 8 pgs.
"U.S. Appl. No. 14/487,730, Preliminary Amendment filed Sep. 16, 2014", 8 pgs.
"U.S. Appl. No. 14/487,730, Response filed Jun. 13, 2016 to Restriction Requirement dated May 31, 2016", 8 pgs.
"U.S. Appl. No. 14/487,730, Response filed Sep. 28, 2016 to Non Final Office Action dated Jun. 28, 2016", 12 pgs.
"U.S. Appl. No. 14/487,730, Restriction Requirement dated May 31, 2016", 6 pgs.
"U.S. Appl. No. 14/749,908, Non Final Office Action dated Sep. 16, 2016", 13 pgs.
"U.S. Appl. No. 14/749,908, Response filed Jul. 8, 2016 to Restriction Requirement dated May 17, 2016", 11 pgs.
"U.S. Appl. No. 14/749,908, Response filed Dec. 12, 2016 to Non Final Office Action dated Sep. 16, 2016", 19 pgs.
"U.S. Appl. No. 14/749,908, Restriction Requirement dated May 17, 2016", 8 pgs.
"Application Serial No. PCT/US2015/037608, Invitation to Pay Additional Fees and Partial Search Report dated Sep. 7, 2015", 6 pgs.
"Geomedic Total Knee Prothesis", Howmedica, Inc., (1975), 4 pgs.
"International Application Serial No. PCT/US2009/048205, International Preliminary Report on Patentability dated Jan. 5, 2011", 4 pgs.
"International Application Serial No. PCT/US2009/048205, International Search Report dated Dec. 11, 2009", 7 pgs.
"International Application Serial No. PCT/US2009/048205, Written Opinion dated Dec. 27, 2010", 9 pgs.
"International Application Serial No. PCT/US2015/037608, International Preliminary Report on Patentability dated Jan. 19, 2017", 12 pgs.
"International Application Serial No. PCT/US2015/037608, International Search Report dated Nov. 24, 2015", 8 pgs.
"International Application Serial No. PCT/US2015/037608, Written Opinion dated Nov. 24, 2015", 10 pgs.
"The Charnley Cobra, The Charnley Knee Prostheses, The Duo/Patella Knee Prostheses", Cintor, Division of Codman, (1975), 4 pgs.
"The Townley Anatomic Knee Replacement", DePuy, 10 pgs.
Levine, Brett R, et al., "Experimental and clinical performance of porous tantalum in orthopedic surgery", Biomaterials, (27), (Sep. 2006), 4671-81.
Pritchett, James W., "BioPro Equalizer Modular Total Knee Replacement", BioPro, Division of Implant Manufacturing and Testing Inc., 19 pgs.
"U.S. Appl. No. 14/749,908, Final Office Action dated Feb. 17, 2017", 12 pgs.
"U.S. Appl. No. 14/749,908, Advisory Action dated Apr. 13, 2017", 3 pgs.
"U.S. Appl. No. 14/749,908, Notice of Allowance dated May 8, 2017", 5 pgs.
"U.S. Appl. No. 14/749,908, Response filed Mar. 31, 2017 to Final Office Action dated Feb. 17, 2017", 13 pgs.
"European Application Serial No. 15736126.2, Response filed Sep. 4, 2017 to Communication pursuant to Rules 161(1) and 162 EPC dated Feb. 21, 2017", 21 pgs.

\* cited by examiner

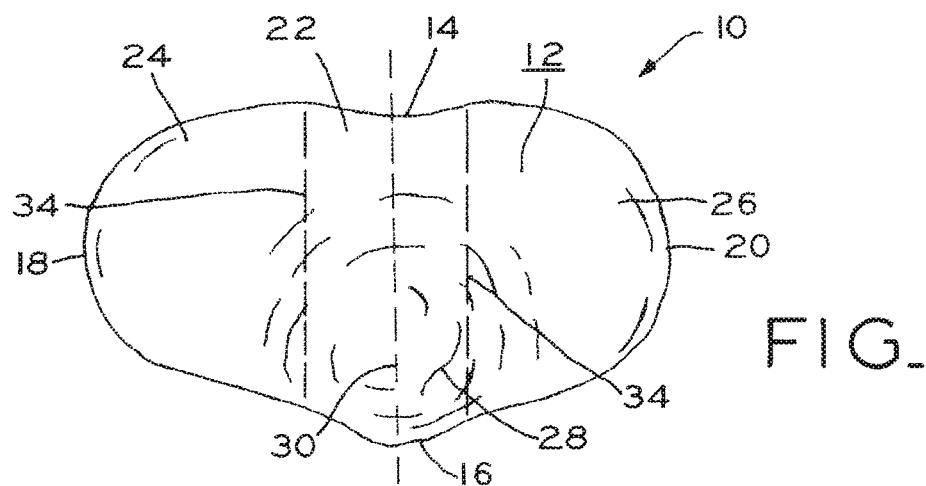
FIG_1
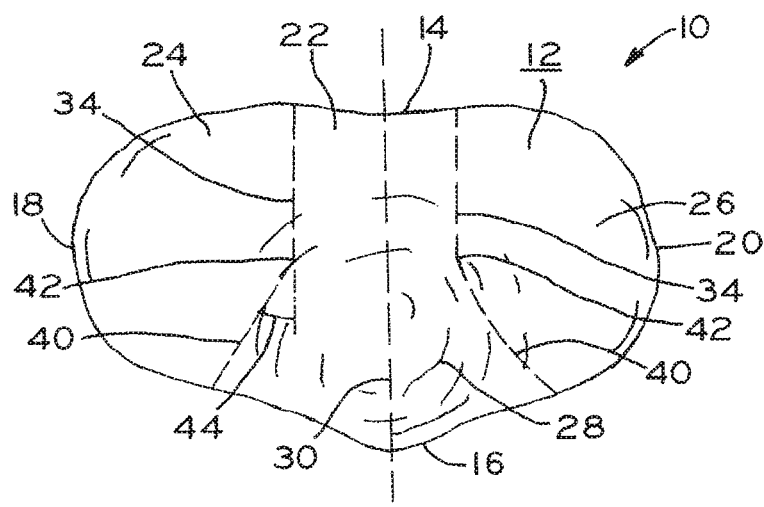
FIG_2
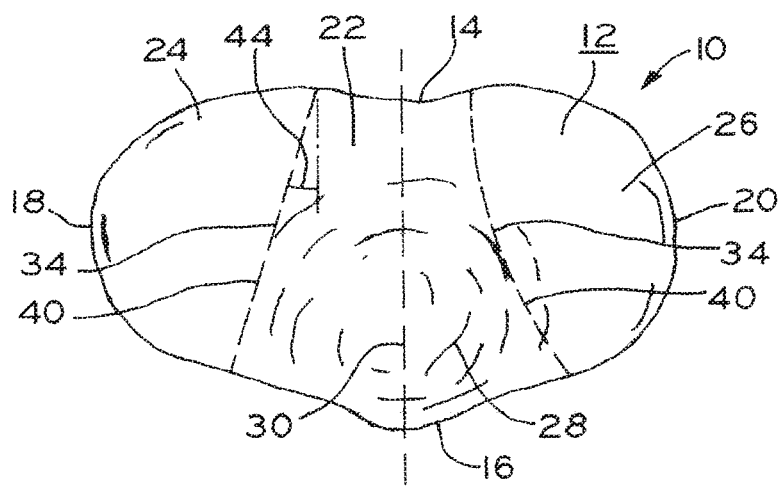
FIG_3

ACL ACCOMMODATING TIBIAL DESIGN

CROSS REFERENCE TO RELATED APPLICATIONS

This application is a continuation of U.S. patent application Ser. No. 14/487,730, filed on Sep. 16, 2014, which is a divisional of U.S. patent application Ser. No. 13/001,442, filed on Mar. 24, 2011, now issued as U.S. Pat. No. 8,864, 836, which is a U.S. National Stage Application based on International Application Serial No. PCT/US2009/048205, filed on Jun. 23, 2009, published on Dec. 30, 2009 as WO 2009/158318 A1, which claims priority from U.S. Provisional Patent Application No. 61/076,206, filed on Jun. 27, 2008 by the same inventors hereof, the disclosures of which are expressly incorporated herein by reference.

BACKGROUND

1. Field of the Invention

The present invention relates to knee arthroplasty, and, more particularly, to surgical methods and a tibial implant for accommodating the anterior cruciate ligament during unicompartmental or bi-unicompartmental knee arthroplasty procedures.

2. Description of the Related Art

Unicompartmental knee arthroplasty and bi-unicompartmental knee arthroplasty procedures involve replacing damaged articular surfaces of a knee joint, while retaining at least the central compartment and the cruciate ligaments. The benefits of both compartmental procedures include the availability of minimally invasive procedures, quicker recovery, and retained knee kinematics compared with total knee arthroplasty procedures.

During a unicompartmental knee arthroplasty procedure, repairs may be made to either the medial compartment or the lateral compartment of the knee, while retaining the other side compartment, the central compartment, and the cruciate ligaments. This procedure requires resection of either the medial compartment or the lateral compartment.

During a bi-unicompartmental knee arthroplasty procedure, repairs may be made to both the medial compartment and the lateral compartment, while still retaining most of the central compartment and the cruciate ligaments. This procedure requires resection of both the medial and lateral compartments. Also, in some cases, a portion of the central compartment is resected to bridge the resected medial and lateral compartments.

The knee joint includes the anterior cruciate ligament (ACL) and the posterior cruciate ligament (PCL). The ACL controls hyperextension of the knee. As the knee joint is positioned in extension, the ACL tightens and functions to prevent hyperextension of the knee. The ACL runs from the posterior side of the femur to the anterior side of the tibia. More specifically, the ACL runs from the posterior side of the femur to a spinous process on the anterior side of the tibia. The spinous process is primarily centered on the proximal tibia, but it also extends into the medial and lateral compartments of the proximal tibia.

Current resection methods often result in removing a significant portion of the spinous process to which the ACL attaches. Generally, enough of the spinous process remains to maintain ACL attachment. However, the strength of the remaining spinous process is significantly undermined, so much so that when the ACL of a knee arthroplasty patient tightens, the spinous process may crack or even break away from the tibia.

SUMMARY

The present invention provides surgical methods for preparing a tibia for a unicompartmental or bi-unicompartmental knee arthroplasty procedure to accommodate the ACL. The tibia includes an articular surface that interacts with a femur, a posterior edge, an anterior edge, a lateral edge, a medial edge, a central compartment, a lateral compartment, and a medial compartment. The tibia also includes a longitudinal axis located within a dividing plane, where the dividing plane extends parallel to a sagittal plane from the posterior edge to the anterior edge of the tibia. The tibia further includes a spinous process to which the ACL attaches. Accommodating the ACL involves preserving the spinous process, and in turn, preserving the natural fixation between the ACL and the spinous process without significantly increasing the risk of damage to the spinous process.

According to an embodiment of the present invention, the method involves making a sagittal cut in the articular surface of the tibia. The sagittal cut extends from the posterior edge to the anterior edge of the tibia, and at least a portion of the sagittal cut extends obliquely to the dividing plane, such that the obliquely extending portion of the sagittal cut extends away from the central compartment of the tibia. The method also involves making a transverse cut beneath the articular surface of the tibia. The transverse cut extends from either a lateral or medial edge of the tibia to the sagittal cut and generally transversely to a longitudinal axis of the tibia. A cut edge forms between the transverse cut and the sagittal cut. The method further involves resecting either a medial or lateral compartment of the tibia along the cut edge, while retaining at least a portion of a central compartment of the tibia and at least a portion of the spinous process to which the ACL attaches.

According to another embodiment of the present invention, the method involves making a sagittal cut in the articular surface of the tibia. The sagittal cut extends from the posterior edge to the anterior edge of the tibia. The method also involves making a transverse cut beneath the articular surface of the tibia. The transverse cut extends from either a lateral or medial edge of the tibia to the sagittal cut and generally transversely to a longitudinal axis of the tibia. A chamfered cut edge forms between the transverse cut and the sagittal cut. The method further involves resecting either a medial or lateral compartment of the tibia along the chamfered cut edge, while retaining at least a portion of a central compartment of the tibia and at least a portion of the spinous process to which the ACL attaches.

The present invention also provides implants for accommodating the ACL during a unicompartmental or bi-unicompartmental knee arthroplasty procedure. The implant includes a body. The implant may further include a bearing layer.

According to an embodiment of the present invention, the body includes a posterior edge, an anterior edge, an inner edge, either a lateral edge or a medial edge, a top surface, and a bottom surface. The posterior, anterior, inner, and lateral or medial edges span the top and bottom surfaces of the body. The inner edge of the body corresponds to the sagittal cut and the cut edge of the tibia, where at least a portion of the sagittal cut extends obliquely to the dividing plane.

According to another embodiment of the present invention, the body includes a posterior edge, an anterior edge, a lateral edge, a medial edge, a first inner edge, a second inner edge, a bridge having an inner edge, a top surface, and a bottom surface. The bridge connects the first and second inner edges. The bridge, the first and second inner edges, and the posterior, anterior, lateral, and medial edges span the top and bottom surfaces of the body. In one form thereof, the bridge inner edge is at least partially chamfered. In another form thereof, the bridge inner edge approaches the anterior edge of the body between the first inner edge and the second inner edge.

By retaining more of the spinous process during a unicompartmental or bi-unicompartmental knee arthroplasty procedure, there is provided a greater surface for ACL attachment. Also, the strength of the spinous process may be greatly improved. This improved strength may avoid the cracking and the breaking away of the spinous process currently seen when the ACL tightens and pulls upon a weakened spinous process. Still, enough of the tibia may be resected to support an implant and the load upon that implant.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 1 is a plan view of the proximal tibia illustrating a surgical method of the present invention;

FIG. 2 is a plan view of the proximal tibia illustrating other surgical methods of the present invention;

FIG. 3 is a plan view of the proximal tibia illustrating still other surgical methods of the present invention;

Corresponding reference characters indicate corresponding parts throughout the several views. The exemplifications set out herein illustrate preferred embodiments of the invention and such exemplifications are not to be construed as limiting the scope of the invention any manner.

DETAILED DESCRIPTION

Figure 4:
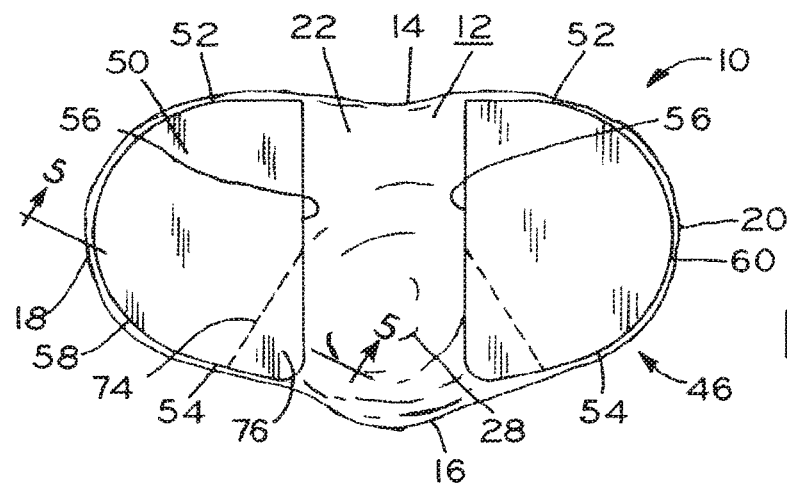
FIG. 4 is a plan view of an implant of the present invention attached to the proximal tibia.

Referring to FIGS. 1-3 and 13-14, tibia 10 of a right leg has articular surface 12 that is configured to articulate with a femur (not shown). Tibia 10 also includes posterior edge 14, anterior edge 16, lateral edge 18, and medial edge 20. Tibia 10 further includes central compartment 22, lateral compartment 24, and medial compartment 26.

As shown in FIG. 1, spinous process 28 is located primarily in central compartment 22 of tibia 10, but may also extend into lateral compartment 24 and medial compartment 26 of tibia 10. Spinous process 28 is a bony prominence of tibia 10 to which the ACL (not shown) attaches.

Figure 13:
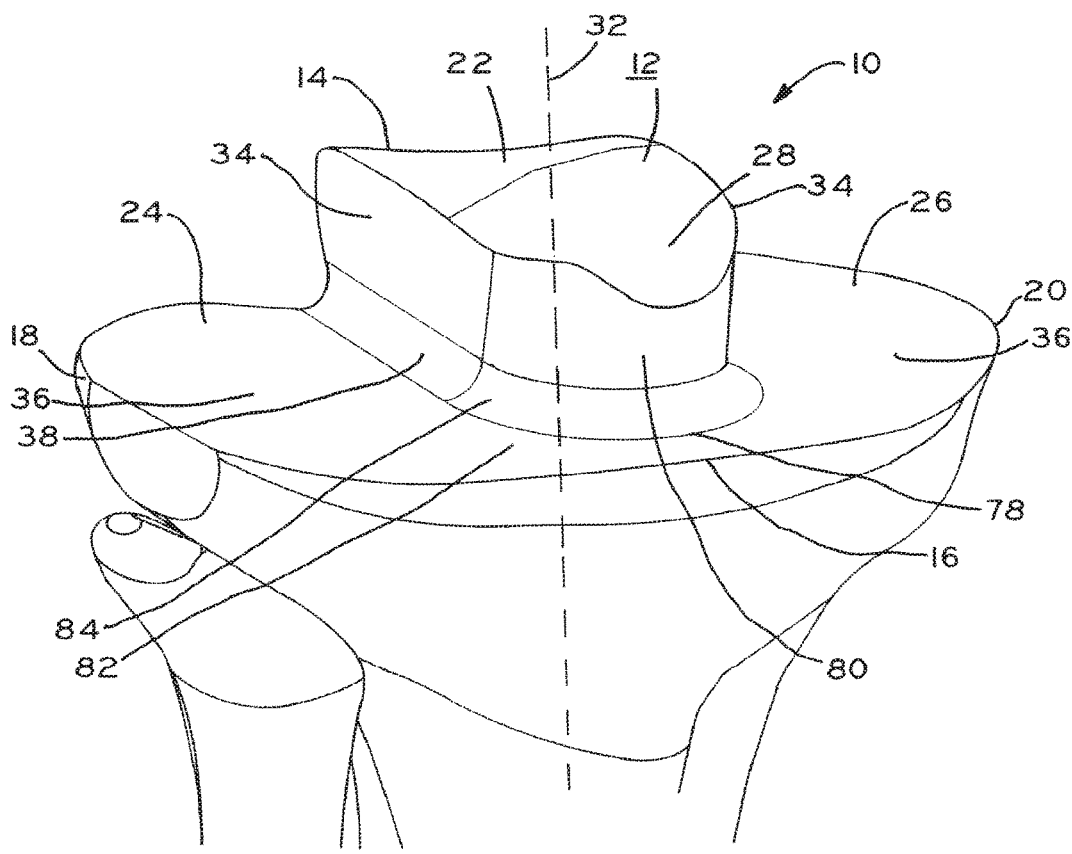
FIG. 13 is an elevational view of the proximal tibia illustrating other surgical methods of the present invention.
Figure 14:
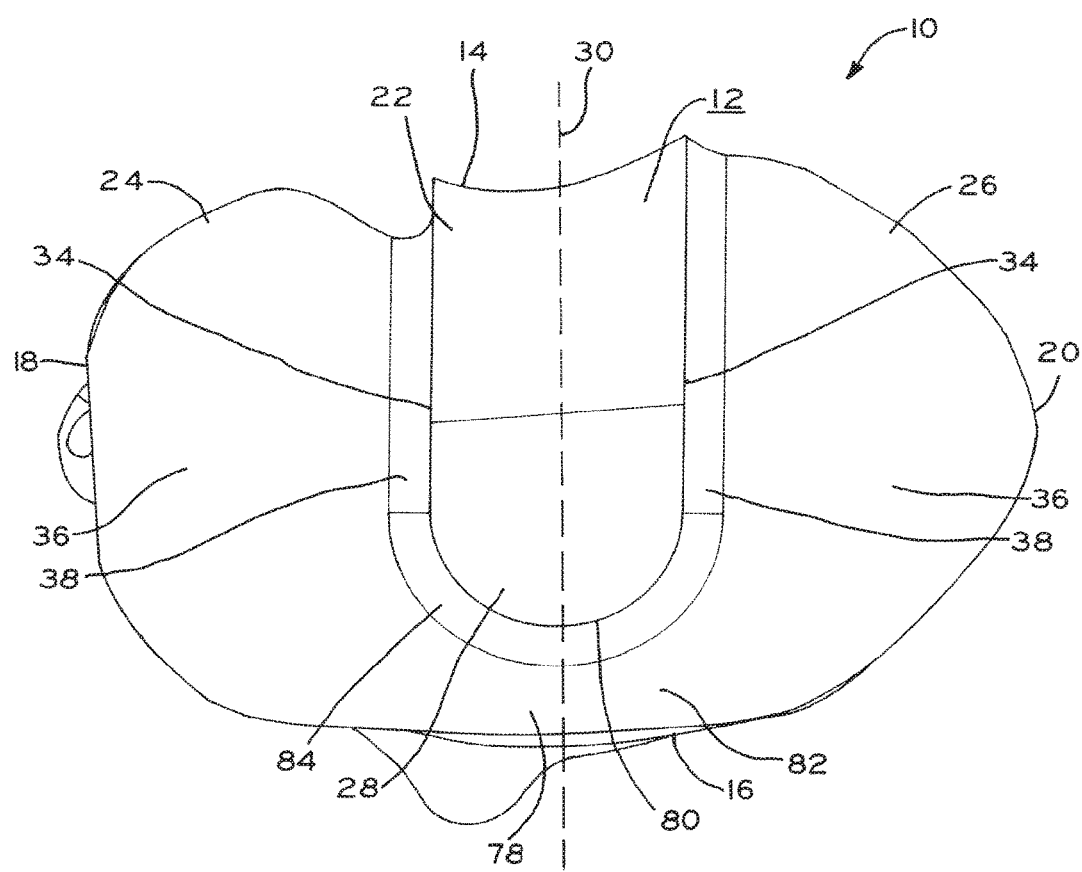
FIG. 14 is a plan view of the proximal tibia of FIG. 14.

As shown in FIGS. 13 and 14, tibia 10 includes longitudinal axis 32. Longitudinal axis 32 is located within dividing plane 30 which runs through tibia 10 in an anterior/posterior direction from anterior edge 16 to posterior edge 14. Dividing plane 30 is substantially parallel to a sagittal plane of the body and is substantially transverse to a horizontal plane of the body.

To prepare tibia 10 for a unicompartmental or bi-unicompartmental knee arthroplasty procedure, either lateral compartment 24 or medial compartment 26, or both, must be resected. The following descriptions may pertain to lateral compartment 24, but the same principles may be applied to medial compartment 26. Resection of lateral compartment 24 involves making sagittal cut 34 and transverse cut 36 into tibia 10. As shown in FIG. 14, sagittal cut 34 is made into articular surface 12 of tibia 10 from posterior edge 14 to anterior edge 16 and between central compartment 22 and lateral compartment 24. As shown in FIG. 13, transverse cut 36 is made beneath articular surface 12 from lateral edge 18 to sagittal cut 34. Transverse cut 36 extends generally transversely to longitudinal axis 32 of tibia 10 and generally parallel to the horizontal plane. A surgeon may use a reciprocating saw and a cutting guide (not shown), a mill and a mill guide (not shown), or another suitable surgical tool to make sagittal cut 34 and transverse cut 36 in tibia 10. For example, when using a mill having a rotating burr, a side edge of the burr may form sagittal cut 34 in tibia 10 and a bottom edge of the burr may form transverse cut 36 in tibia 10. Sagittal cut 34 and transverse cut 36 intersect at cut edge 38. After sagittal cut 34 and transverse cut 36 are made, lateral compartment 24 may be resected from tibia 10 along cut edge 38.

Figure 5:
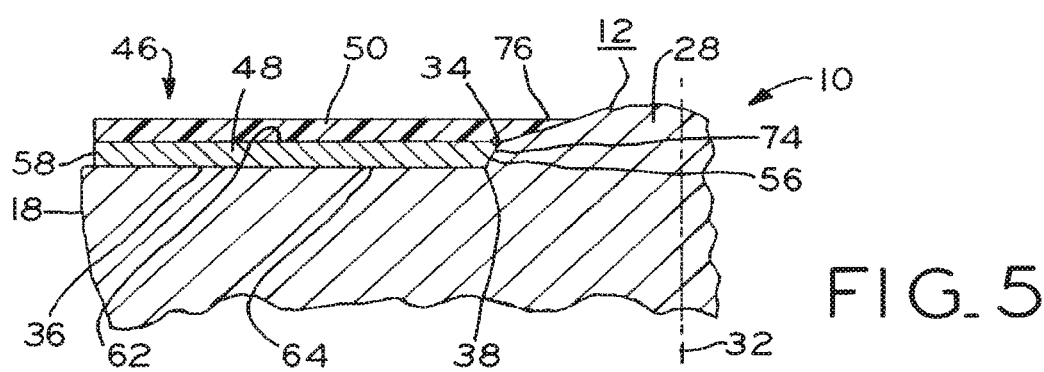
FIG. 5 is a cross-sectional view of the implant of FIG. 4, taken along line 5-5 of FIG. 4.
Figure 7:
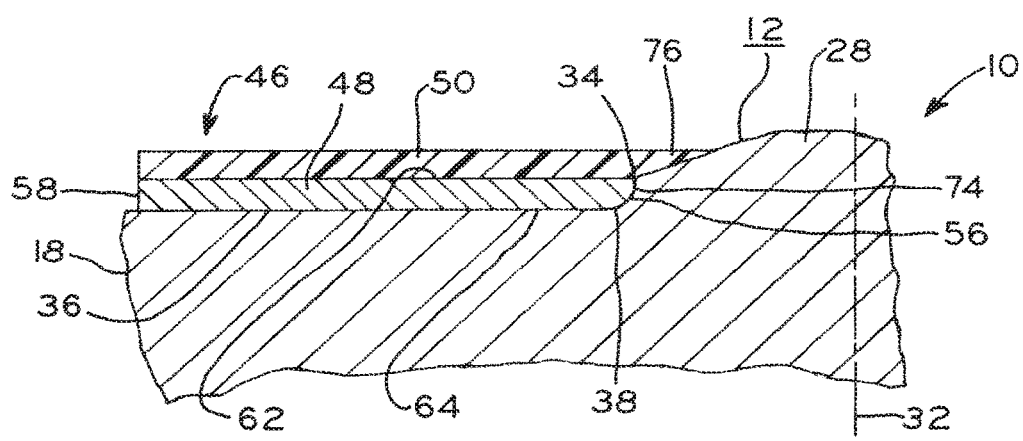
FIG. 7 is a cross-sectional view similar to FIG. 5 of another implant of the present invention.
Figure 8:
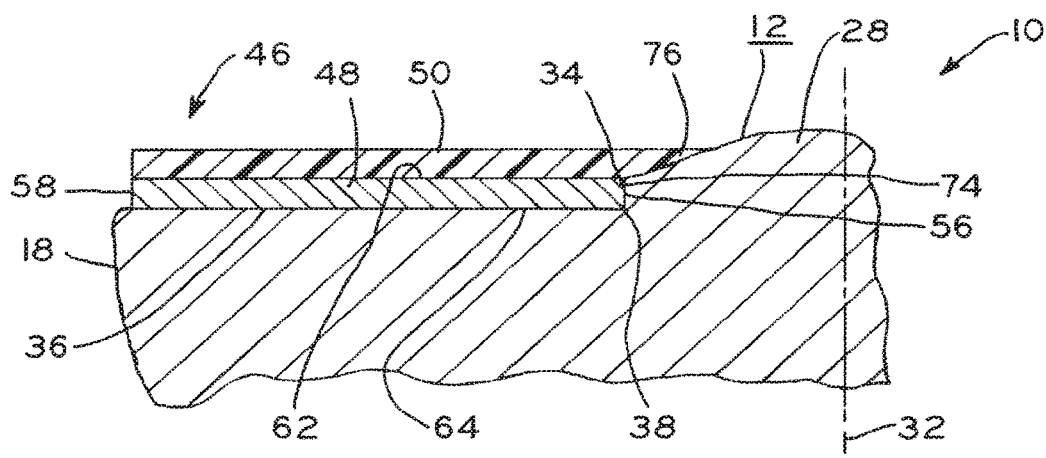
FIG. 8 is a cross-sectional view similar to FIG. 5 of still another implant of the present invention.

According to a first embodiment of the present invention, as shown in FIGS. 1 and 13-14, sagittal cut 34 may extend substantially parallel to dividing plane 30 from posterior edge 14 to anterior edge 16. To accommodate spinous process 28, cut edge 38 between sagittal cut 34 and transverse cut 36 may be at least partially chamfered. In an exemplary embodiment of the present invention, cut edge 38 is at least partially chamfered in the area adjacent to spinous process 28. For purposes of this disclosure, cut edge 38 is "chamfered" whenever sagittal cut 34 and transverse cut 36 intersect to form an angle that is greater than 90 degrees. For example, as illustrated in FIG. 5, a chamfered cut edge 38 may be formed between sagittal cut 34 that is angled away from longitudinal axis 32 and an essentially horizontal transverse cut 36. For purposes of this disclosure, cut edge 38 is also "chamfered" whenever sagittal cut 34 and transverse cut 36 intersect to form a rounded or curved cut edge 38, as illustrated in FIGS. 7 and 13. Compared to current resection methods, both chamfering techniques retain more bone at the base of spinous process 28 and avoid undercutting spinous process 28. Cut edge 38 may be chamfered by using, for example, a cutting guide (not shown) that matches the desired shapes of sagittal cut 34 and transverse cut 36.

According to another embodiment of the present invention, to further accommodate spinous process 28, sagittal cut 34 may deviate from a path essentially parallel to dividing plane 30. In other words, at least a portion 40 of sagittal cut 34 may extend obliquely to dividing plane 30, thereby extending away from central compartment 22 and away from spinous process 28.

As shown in FIG. 2, sagittal cut 34 may extend substantially parallel to dividing plane 30 from posterior edge 14 of tibia 10 to deflection point 42 spaced between posterior edge 14 and anterior edge 16 of tibia 10. Between deflection point 42 and anterior edge 16 of tibia 10, sagittal cut 34 may extend obliquely to dividing plane 30. In one form thereof, illustrated in lateral compartment 24 of FIG. 2, obliquely extending portion 40 may extend linearly between deflection point 42 and anterior edge 16 of tibia 10, forming acute angle 44 between dividing plane 30 and obliquely extending portion 40, where acute angle 44 is greater than 0 degrees. For example, acute angle 44 may be as small as approximately 1 degree, 2 degrees, 3 degrees, 4 degrees, or 5 degrees or as large as approximately 10 degrees, 15 degrees, 20 degrees, 25 degrees, 30 degrees, or more. A single deflection point 42 located approximately midway between posterior edge 14 and anterior edge 16 of tibia 10 is illustrated in FIG. 2, but it is also within the scope of the present invention that deflection point 42 may be located nearer to either posterior edge 14 or anterior edge 16, and that there may be multiple deflection points 42. In that form, obliquely extending portion 40 may include any number of substantially linear, non-collinear cuts that intersect at multiple deflection points 42. In another form thereof, illustrated in medial compartment 26 of FIG. 2, obliquely extending portion 40 may curve from deflection point 42 to anterior edge 16 of tibia 10.

As shown in FIG. 3, entire sagittal cut 34 may extend obliquely to dividing plane 30 from posterior edge 14 to anterior edge 16 of tibia 10. In one form thereof, illustrated in lateral compartment 24 of FIG. 3, obliquely extending portion 40 of sagittal cut 34 may extend linearly from posterior edge 14 to anterior edge 16 of tibia 10, forming acute angle 44 between dividing plane 30 and obliquely extending portion 40, where acute angle 44 is greater than 0 degrees. For example, acute angle 44 may be as small as approximately 1 degree, 2 degrees, 3 degrees, 4 degrees, or 5 degrees or as large as approximately 10 degrees, 15 degrees, 20 degrees, 25 degrees, 30 degrees, or more. In another form thereof, illustrated in medial compartment 26 of FIG. 3, obliquely extending portion 40 may curve from posterior edge 14 to anterior edge 16 of tibia 10.

According to yet another embodiment of the present invention, to even further accommodate spinous process 28, portion 40 of sagittal cut 34 may extend obliquely to dividing plane 30 and, in addition, cut edge 38 may be at least partially chamfered. In an exemplary embodiment of the present invention, cut edge 38 is at least partially chamfered in the area adjacent to spinous process 28. Both techniques are discussed in more detail above.

Referring again to FIGS. 13 and 14, to prepare tibia 10 for a bi-unicompartmental knee arthroplasty procedure, both lateral compartment 24 and medial compartment 26 must be resected. The resection of lateral compartment 24 and medial compartment 26 can be performed in accordance with the teachings set forth above. Further, during a bi-unicompartmental knee arthroplasty procedure, a portion of central compartment 22, referred to herein as bridge portion 78, may be resected to join resected lateral compartment 24 and resected medial compartment 26. Bridge portion 78 may be located in central compartment 22 near anterior edge 16 of tibia 10. By resecting bridge portion 78, a single tibial implant 46 that spans resected lateral compartment 24, resected bridge portion 78 of central compartment 22, and resected medial compartment 26 can be utilized, as described in more detail below.

Referring still to FIGS. 13 and 14, resection of bridge portion 78 of central compartment 22 involves making vertical bridge cut 80 and horizontal bridge cut 82 into tibia 10. Vertical bridge cut 80 is made into articular surface 12 of tibia 10 and extends from sagittal cut 34 in lateral compartment 24 to sagittal cut 34 in medial compartment 26. Horizontal bridge cut 82 is made beneath articular surface 12 and extends from anterior edge 16 of tibia to vertical bridge cut 80. Horizontal bridge cut 82 also extends from transverse cut 36 in lateral compartment 24 to transverse cut 36 in medial compartment 26. Like transverse cut 36, horizontal bridge cut 82 extends generally transversely to longitudinal axis 32 of tibia 10 and generally parallel to the horizontal plane of the body. Vertical bridge cut 80 and horizontal bridge cut 82 intersect at bridge cut edge 84. After vertical bridge cut 80 and horizontal bridge cut 82 are made, bridge portion 78 of central compartment 22 may be resected from tibia 10 along bridge cut edge 84.

According to an embodiment of the present invention, to accommodate spinous process 28, bridge cut edge 84 may be at least partially chamfered. Similar to the chamfering of cut edge 38, bridge cut edge 84 is "chamfered" whenever vertical bridge cut 80 and horizontal bridge cut 82 intersect to form an angle that is greater than 90 degrees. Bridge cut edge 84 is also "chamfered" whenever vertical bridge cut 80 and horizontal bridge cut 82 intersect to form a rounded or curved bridge cut edge 84, as illustrated in FIGS. 1 and 14. Compared to current resection methods, both chamfering techniques retain more bone at the base of spinous process 28 and avoid under-cutting spinous process 28.

According to another embodiment of the present invention, to further accommodate spinous process 28, vertical bridge cut 80 may extend away from spinous process 28 and toward anterior edge 16 of tibia 10 between lateral compartment 24 and medial compartment 26 of tibia 10. For example, as illustrated in FIGS. 13-14, as vertical bridge cut 80 approaches dividing plane 30, vertical bridge cut 80 curves toward anterior edge 16 of tibia 10. Vertical bridge cut 80 need not extend linearly from lateral compartment 24 to medial compartment 26. Vertical bridge cut 80 may be shaped by, for example, milling tibia 10 or cutting tibia 10 with a reciprocating saw blade.

According to yet another embodiment of the present invention, to even further accommodate spinous process 28, vertical bridge cut 80 may curve away from spinous process 28 and, in addition, bridge cut edge 84 may be at least partially chamfered. Both techniques are discussed in more detail above.

Figures 9, 10:
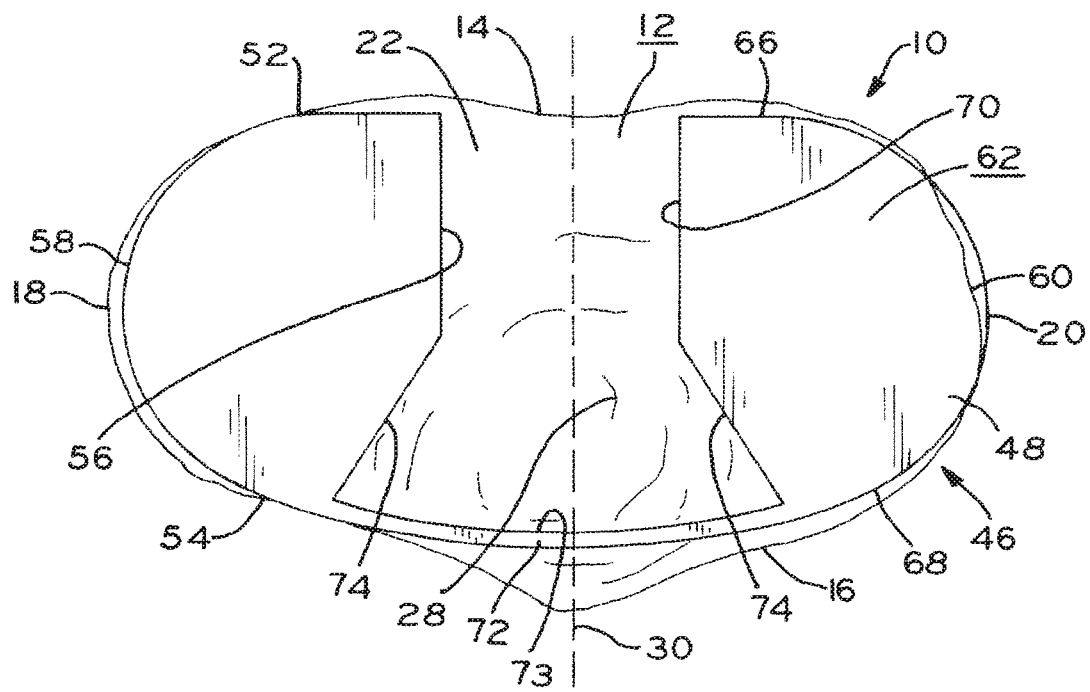
FIG. 9 is a plan view of the implant of FIG. 6 attached to the proximal tibia.
FIG. 10 is a plan view of another implant of the present invention.

Referring next to FIGS. 4-12, tibial implant 46 is provided for use with the surgical methods set forth above. According to an exemplary embodiment of the present invention, tibial implant 46 is contoured to mimic the size and shape of tibia 10 after tibia 10 is resected using at least one of the surgical methods set forth above. Implant 46 may include body 48 and bearing layer 50. As illustrated in FIGS. 4 and 9, body 48 of implant 46 is attached to tibia 10 of a right leg, but the same principles discussed herein may be applied to a left leg.

Body 48 may be constructed of any biocompatible ceramic or metal, including, but not limited to, titanium, a titanium alloy, cobalt chromium, cobalt chromium molybdenum, porous tantalum, or a highly porous biomaterial. A highly porous biomaterial is useful as a bone substitute and as cell and tissue receptive material.

A highly porous biomaterial may have a porosity as low as 55, 65, or 75 percent and as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of body 48 of implant 46 to tibia 10.

The porous tantalum structure may be made in a variety of densities to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone to provide an improved matrix for bone ingrowth and mineralization.

In one form thereof, illustrated in FIGS. 4, 5, 7, and 8, body 48 has first posterior edge 52, first anterior edge 54, first inner edge 56, either lateral edge 58 or medial edge 60, top surface 62, and bottom surface 64. First posterior edge 52, first anterior edge 54, first inner edge 56, and either lateral edge 58 or medial edge 60 span top surface 62 and bottom surface 64 of body 48. Body 48, as set forth in this first embodiment, may be used during unicompartmental and bi-unicompartmental knee arthroplasty procedures. During a unicompartmental knee arthroplasty procedure, a single body 48 may be implanted into either resected compartment of tibia 10—either lateral compartment 24 or medial compartment 26. During a bi-unicompartmental knee arthroplasty procedure, body 48 may be implanted into lateral compartment 24, and another body 48 may be implanted into medial compartment 26, as shown in FIG. 4. Body 48 may be secured to lateral compartment 24 of tibia 10 such that: bottom surface 64 of body 48 corresponds to transverse cut 36 of tibia 10 in lateral compartment 24; first inner edge 56 of body 48 corresponds to sagittal cut 34 and cut edge 38 of tibia 10 in lateral compartment 24; first posterior edge 52 of body 48 corresponds to posterior edge 14 of tibia 10; first anterior edge 54 of body 48 corresponds to anterior edge 16 of tibia 10; and lateral edge 58 of body 48 corresponds to lateral edge 18 of tibia 10. Similarly, body 48 may be secured to medial compartment 26 of tibia 10 such that: bottom surface 64 of body 48 corresponds to transverse cut 36 of tibia 10 in medial compartment 26; first inner edge 56 of body 48 corresponds to sagittal cut 34 and cut edge 38 of tibia 10 in medial compartment 26; first posterior edge 52 of body 48 corresponds to posterior edge 14 of tibia 10; first anterior edge 54 of body 48 corresponds to anterior edge 16 of tibia 10; and medial edge 60 of body 48 corresponds to medial edge 20 of tibia 10.

In another form thereof, illustrated in FIGS. 6 and 9-12, body 48 has both first posterior edge 52 and second posterior edge 66, both first anterior edge 54 and second anterior edge 68, both first inner edge 56 and second inner edge 70, bridge 72 connecting first inner edge 56 and second inner edge 70, bridge 72 having its own bridge inner edge 73, both lateral edge 58 and medial edge 60, top surface 62, and bottom surface 64. First and second posterior edges 52 and 66, first and second anterior edges 54 and 68, first and second inner edges 56 and 70, bridge 72, bridge inner edge 73, lateral edge 58, and medial edge 60 span top surface 62 and bottom surface 64 of body 48. Bridge 72, which connects first inner edge 56 and second inner edge 70, may also connect first anterior edge 54 and second anterior edge 68. Body 48, as set forth in this second embodiment, is designed for use during a bi-unicompartmental knee arthroplasty procedure. Body 48 may be implanted into both resected compartments of tibia 10—both lateral compartment 24 and medial compartment 26—with bridge 72 spanning bridge portion 78 of central compartment 22. More specifically, body 48 may be secured to tibia 10 such that: bottom surface 64 of body 48 corresponds to transverse cut 36 in lateral compartment 24, transverse cut 36 in medial compartment 26, and horizontal bridge cut 82 in central compartment 22; first inner edge 56 of body 48 corresponds to sagittal cut 34 and cut edge 38 in lateral compartment 24; second inner edge 70 of body 48 corresponds to sagittal cut 34 and cut edge 38 in medial compartment 26; bridge inner edge 73 of body 48 corresponds to vertical bridge cut 80 and bridge cut edge 84 in central compartment 22; first posterior edge 52 and second posterior edge 66 of body 48 correspond to posterior edge 14 of tibia 10; first anterior edge 54 and second anterior edge 68 of body 48 correspond to anterior edge 16 of tibia 10; lateral edge 58 of body 48 corresponds to lateral edge 18 of tibia 10; and medial edge 60 of body 48 corresponds to medial edge 20 of tibia 10.

Body 48 may be secured to tibia 10 by any method known in the art. An exemplary method of attachment involves using an adhesive, which may not only provide a secure connection between body 48 and tibia 10, but may also strengthen tibia 10. The adhesive may be any known medical grade adhesive having sufficient strength to secure body 48 to tibia 10, including, but not limited to, bone cement, light curable acrylic adhesives, acrylic adhesives, cyanoacrylate adhesives, silicone adhesives, urethane adhesives, and epoxy adhesives.

Figure 6:
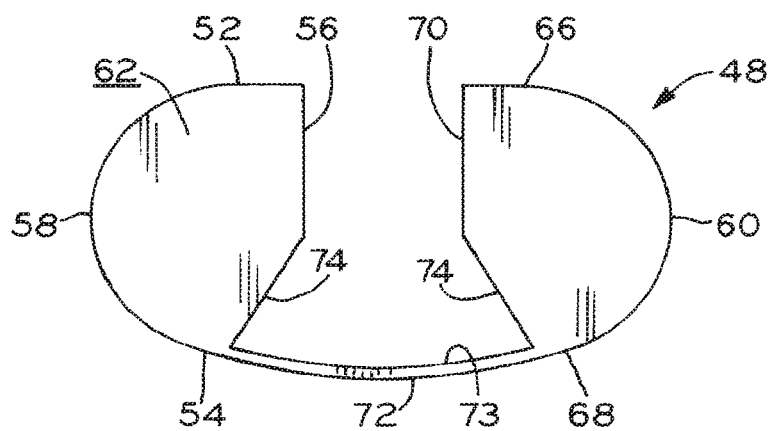
FIG. 6 is a plan view of another implant of the present invention.

According to an embodiment of the present invention, as shown in FIGS. 4, 6, and 9, first inner edge 56 (and second inner edge 70 if applicable) of body 48 correspond to sagittal cut 34 of tibia 10, where at least a portion 40 of sagittal cut 34 extends obliquely to dividing plane 30. Therefore, once implanted, at least a portion 74 of first inner edge 56 (and second inner edge 70 if applicable) of body 48 also extends obliquely to dividing plane 30, thereby extending away from central compartment 22 and away from spinous process 28.

Figure 11:
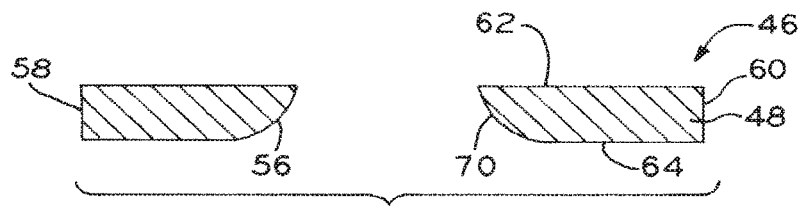
FIG. 11 is cross-sectional view of the implant of FIG. 10, taken along line 11-11 of FIG. 10.

According to another embodiment of the present invention, as shown in FIGS. 5, 7 and 11, first inner edge 56 (and second inner edge 70 if applicable) of body 48 correspond to cut edge 38 of tibia 10, where at least a portion of cut edge 38 is chamfered. In other words, at least a portion of first inner edge 56 (and second inner edge 70 if applicable) of body 48 are also chamfered. For purposes of this disclosure, first inner edge 56 and second inner edge 70 of body 48 are "chamfered" whenever first inner edge 56 or second inner edge 70 and bottom surface 64 of body 48 form an angle that is greater than 90 degrees. For example, as illustrated in FIG. 5, first inner edge 56 of body 48 may be angled away from longitudinal axis 32. For purposes of this disclosure, first inner edge 56 and second inner edge 70 of body 48 are also "chamfered" whenever the edges are rounded, as illustrated in FIGS. 7 and 11.

According to yet another embodiment of the present invention, bridge inner edge 73 of body 48 corresponds to vertical bridge cut 80 of tibia 10, where vertical bridge cut 80 extends away from spinous process 28 and toward anterior edge 16 of tibia 10. For example, as shown in FIGS. 6 and 9-10, bridge inner edge 73 of body 48 does not extend linearly between first inner edge 56 and second inner edge 70 of body 48. Rather, once implanted, bridge inner edge 73 curves away from spinous process 28 and toward anterior edge 16 of tibia 10 near dividing plane 30.

Figure 12:
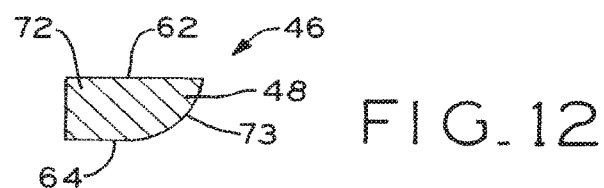
FIG. 12 is cross-sectional view of the implant of FIG. 10, taken along line 12-12 of FIG. 10.

According to still yet another embodiment of the present invention, bridge inner edge 73 of body 48 corresponds to bridge cut edge 84 of tibia 10, where at least a portion of bridge cut edge 84 is chamfered. In other words, at least a portion of bridge inner edge 73 of body 48 is also chamfered. For purposes of this disclosure, bridge inner edge 73 of body 48 is "chamfered" whenever bridge inner edge 73 and bottom surface 64 of body 48 form an angle that is greater than 90 degrees. Bridge inner edge 73 of body 48 is also "chamfered" whenever the edge is rounded, as illustrated in FIG. 12.

As mentioned above, implant 46 may include bearing layer 50. More specifically, implant 46 may include bearing layer 50 attached to top surface 62 of body 48. It is within the scope of the present invention that body 48 and bearing layer 50 of implant 46 may be integrally formed of a single material or more than one material. Bearing layer 50 is configured to interact with a femoral component (not shown).

Bearing layer 50 may be constructed of a polymer, including, but not limited to, a poly ether ether ketone, fiber reinforced poly ether ether ketone, ultrahigh molecular weight polyethylene, crosslinked ultrahigh molecular weight polyethylene, or polyether ketone ether ether ketone. Advantageously, by utilizing a rigid material for body 48, such as a metal, with a more resilient material for bearing layer 50, such as a polymer, wear of the femoral component (not shown) may be reduced.

According to yet another exemplary embodiment of the present invention, as shown in FIGS. 4-8, bearing layer 50 may extend peripherally at least partially beyond first inner edge 56 of body 48, second inner edge 70 of body 48, and/or bridge inner edge 73 of body 48, thereby forming bearing overhang 76. Bearing overhang 76 may protect portions of articular surface 12 and spinous process 28 that remain after resection. Bearing overhang 76 is especially useful for resections performed with sagittal cut 34 that includes obliquely extending portion 40, because greater portions of articular surface 12 and spinous process 28 remain, as compared to resections performed with sagittal cut 34 that extends essentially parallel to dividing plane 30. Bearing overhang 76 may be spaced away from tibia 10, or bearing overhang 76 may abut tibia 10.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An implant adapted for attachment to a tibia during knee arthroplasty to accommodate the anterior cruciate ligament, the tibia having medial and lateral compartments resected along an intercondylar eminence that is disposed between the medial and lateral compartments, the implant comprising:
a medial implant body having a medial posterior edge, a medial anterior edge, a medial inner edge, a medial outer edge, a medial top surface, and a medial bottom surface, at least a portion of the medial inner edge including a medial chamfer that forms an obtuse angle with the medial bottom surface; and
a lateral implant body having a lateral posterior edge, a lateral anterior edge, a lateral inner edge, a lateral outer edge, a lateral top surface, and a lateral bottom surface, at least a portion of the lateral inner edge including a lateral chamfer that forms an obtuse angle with the lateral bottom surface;
wherein upon attachment of the medial and lateral implant bodies to the tibia, the medial and lateral chamfers are configured to be positioned adjacent to corresponding chamfered portions of the intercondylar eminence.

2. The implant of claim 1, wherein the medial chamfer and the lateral chamfer comprise planar surfaces.

3. An implant adapted for attachment to a tibia during knee arthroplasty to accommodate the anterior cruciate ligament, the tibia having medial and lateral compartments resected along an intercondylar eminence that is disposed between the medial and lateral compartments, the implant comprising:
a medial implant body having a medial posterior edge, a medial anterior edge, a medial inner edge, a medial outer edge, a medial top surface, and a medial bottom surface, at least a portion of the medial inner edge including a medial chamfer;
a lateral implant body having a lateral posterior edge, a lateral anterior edge, a lateral inner edge, a lateral outer edge, a lateral top surface, and a lateral bottom surface, at least a portion of the lateral inner edge including a lateral chamfer; and
a bridge extending between the medial implant body and the lateral implant body;
wherein upon attachment of the implant to the tibia, the medial and lateral chamfers are configured to be positioned adjacent to corresponding chamfered portions of the intercondylar eminence.

4. The implant of claim 3, wherein the medial chamfer and the lateral chamfer comprise rounded surfaces.

5. The implant of claim 3, wherein the medial chamfer comprises a planar surface extending at a first oblique angle between the medial top surface and the medial bottom surface, and wherein the lateral chamfer comprises a planar surface extending at a second oblique angle between the lateral top surface and the lateral bottom surface.

6. The implant of claim 5, wherein the first and second oblique angles are the same.

7. The implant of claim 3, wherein the bridge further comprises a bridge top surface, a bridge bottom surface, and a bridge inner edge positionable adjacent to the intercondylar eminence.

8. The implant of claim 7, wherein at least a portion of the bridge inner edge includes a bridge chamfer configured to be positioned adjacent to a corresponding chamfered portion of the intercondylar eminence upon attachment of the implant to the tibia.

9. The implant of claim 8, wherein the bridge inner edge is curved in a medial-lateral direction.

10. The implant of claim 8, wherein the bridge chamfer comprises a rounded surface.

11. The implant of claim 8, wherein the bridge chamfer comprises a planar surface extending at an oblique angle between the bridge top surface and the bridge bottom surface.

12. The implant of claim 8, wherein the medial chamfer, the lateral chamfer, and the bridge chamfer intersect to form one continuous chamfered inner edge of the implant.

13. The implant of claim 3, wherein the medial implant body, the lateral implant body, and the bridge define a generally U-shaped implant configuration.

14. An implant adapted for attachment to a tibia during knee arthroplasty to accommodate the anterior cruciate ligament, the tibia having medial and lateral compartments resected along an intercondylar eminence that is disposed between the medial and lateral compartments, the implant comprising:

a body including a medial portion and a lateral portion joined together by a bridge, the body having a posterior edge, an anterior edge, an inner edge, an outer edge, a top surface, and a bottom surface, the posterior, anterior, inner, and outer edges spanning the top and bottom surfaces of the body, wherein at least a portion of the inner edge of the body includes a chamfer between the top surface and the bottom surface, and wherein upon attachment of the implant to the tibia, the chamfer is configured to abut a corresponding chamfered portion of the intercondylar eminence.

15. The implant of claim 14, wherein the chamfer comprises a rounded surface.

16. The implant of claim 14, wherein the chamfer comprises a planar surface extending at an oblique angle between the top surface and the bottom surface.

17. The implant of claim 14, wherein the medial portion, the lateral portion, and the bridge define a generally U-shaped implant configuration.

18. The implant of claim 14, further comprising a bearing securable to the body.

* * * * *

UNITED STATES PATENT AND TRADEMARK OFFICE
CERTIFICATE OF CORRECTION

PATENT NO. : 10,271,955 B2
APPLICATION NO. : 15/427280
DATED : April 30, 2019
INVENTOR(S) : Hodorek et al.

Page 1 of 1

It is certified that error appears in the above-identified patent and that said Letters Patent is hereby corrected as shown below:

On the Title Page

In "Related U.S. Application Data", in Column 1, Line 1, delete "(60)" and insert --(63)-- therefor On page 2, in Column 2, under "Other Publications", Line 34, delete "Prothesis"," and insert --Prosthesis",-- therefor Signed and Sealed this
Twenty-first Day of April, 2020

Andrei Iancu
*Director of the United States Patent and Trademark Office*